United States Patent [19]

Meier et al.

[11] Patent Number: 4,986,534

[45] Date of Patent: Jan. 22, 1991

[54] COMPUTERIZED BIOMECHANICAL ANALYSIS SYSTEM

[75] Inventors: Robert H. Meier, Ann Arbor; Jerry E. Seel; Gary W. Gray, both of Adrian, all of Mich.

[73] Assignee: Camp International, Inc., Jackson, Mich.

[21] Appl. No.: 459,970

[22] Filed: Jan. 2, 1990

[51] Int. Cl.⁵ ...................... A63B 23/08; A63B 23/10; A63B 22/14

[52] U.S. Cl. ...................................... 272/96; 272/146; 272/DIG. 5

[58] Field of Search ............. 272/96, 70, 146, DIG. 5; 125/25 R, 25 B; 73/379

[56] References Cited

U.S. PATENT DOCUMENTS

| | | | |
|---|---|---|---|
| 4,014,398 | 3/1977 | Gresko | 128/782 |
| 4,452,447 | 6/1984 | Lepley et al. | 272/96 |
| 4,605,220 | 8/1986 | Troxel | 272/96 |
| 4,635,932 | 1/1987 | Dewees | 272/96 |
| 4,653,748 | 3/1987 | Seel et al. | 272/96 |
| 4,709,917 | 12/1987 | Yang | 272/DIG. 5 |
| 4,735,410 | 4/1988 | Nobuta | 272/DIG. 5 |
| 4,927,138 | 5/1990 | Ferrari | 272/70 |

*Primary Examiner*—Robert Bahr
*Assistant Examiner*—Lynne A. Reichard
*Attorney, Agent, or Firm*—Beaman & Beaman

[57] ABSTRACT

The invention pertains to a method and apparatus for biomechanically analyzing the physical characteristics of the lower extremety including hip, knee and ankle joints and the muscles and ligaments, and the functioning thereof. A frame includes a weight sensing platform and a foot support in the form of a disc is mounted above the platform for nutation about a vertical axis. The periphery of the disc engages the platform, and actuates platform switches whereby a patient standing upon the disc with one foot may angularly displace the disc in a nutating manner applying weight to the platform through the disc periphery, and recording apparatus in the form of computerized data and a visual display permits analysis of the application of weight to the platform. The disc may be selectively vertically adjustable relative to the platform to vary the analysis characteristics.

24 Claims, 6 Drawing Sheets

COMPUTERIZED BIOMECHANICAL ANALYSIS SYSTEM

BACKGROUND OF THE INVENTION

The lower limb functions as an integrated unit during activity, and in a healthy lower limb the hip, knee, ankles, toes and the muscles, ligaments and other dynamic functional parts of the lower limb act as a closed kinetic chain. To return an injured joint to its previous level of performance it must also perform as an integrated unit in positions of function while undergoing rehabilitation. Isolated testing and rehabilitation address only the isolated injured joint, while the progressive functional integration of that joint may be even more important than its isolated condition.

In order to analyze the rehabilitation of a healing lower extremity joint analysis of the weight distribution of which the foot is capable of attaining is significant, and devices have been proposed for such purpose as shown in U.S. Pat. Nos. 2,095,268 and 4,014,398. Exercise devices for the ankle and lower leg are known as shown in U.S. Pat. No. 4,635,932, and it is known to use computerized analysis systems for analyzing and recording forces acting on the human foot, such as shown in U.S. Pat. No. 4,452,447. However, previously known devices are not of such sophistication and construction as to provide both functional closed-chain assessment and rehabilitation of the lower limb and produce objective data regarding the functional performance of the lower extremity.

A widely recognized method of closed-chain dynamic rehabilitation for the lower extremity is the Biomechanical Ankle Platform System (BAPS), and this device permits rehabilitation of the lower limb as a unit wherein the lower extremity is able to repair itself in a functional, integrated manner. The BAPS system is described in U.S. Pat. No. 4,653,748, and the foot support disc disclosed in this patent also appears in U.S. Pat. No. Des. 278,924.

It is an object of the invention to provide a biomechanical analysis system for the lower extremity which permits functional closed-chain assessment and rehabilitation, and complete readily analyzable data is instantly produced which permits rapid evaluation.

A further object of the invention is to provide a method for biomechanical analysis of the lower limb wherein the method is based on the principles of dynamic closed chain rehabilitation used with the BAPS system and wherein rapid assessment of the condition of the lower extremity is possible and objective data instantaneously obtained with respect to the analysis.

Yet another object of the invention is to provide a method for biomechanical analysis of the lower extremity capable of analyzing the functioning of the lower extremity as a integrated unit while simultaneously undergoing rehibilitation.

An additional object of the invention is to provide a biomechanical analysis system for the lower extremity wherein an electronic assessment output is achieved with the use of the apparatus and an instant analysis of the functional performance of the extremity is provided and the patient may view this performancy on a display screen permitting an immediate visualization of the state of progress and quantitative analysis.

Another object of the invention is to provide a biomechanical apparatus for the lower extremity which is easily usable by the relatively unskilled operator, is easily used by the patient, and is adjustable though a wide range of operating characteristics to permit immediate analysis by the patient of his progress.

In the practice of the inventive concepts apparatus is employed which permits visual and recordable evaluation of the exercising and rehabilitation when utilizing the BAPS system for lower extremity rehabilitation. The invention contemplates a method of lower extremity biomechanical analysis which is immediate and complete and permits immediate analysis and recognition of various lower extremity conditions such as equinas, supinatory and pronatory foot conditions, and permits analysis of pressures of which the lower limb is capable of exerting anterolaterally, anteromedially, posterolaterally and posteromedially and the flexibility of the lower limb and ankle may be immediately analyzed, for instance, a lack of dorsiflexion may be immediately discerned. The apparatus permits a more definitive assessment of the lower extremity than was heretofore available, and with the use of the invention a more explicit therapy program can be devised which is more efficient than previously achievable.

The apparatus of the biomechanical analysis system of the invention includes a frame of a generally rectangularly configuration having patient hand rails and supports vertically extending thereabove. A weight sensing platform is mounted upon the frame supported upon a plurality of accurate, spaced weight measuring sensors whereby the sensors are capable of accurately determining the presence of weight as applied to the platform at a given location and produce a proportional electrical signal.

A vertically extending shaft passes through the platform without connection thereto, and the upper end of the shaft is provided with universal joint structure for supporting a foot support disc having a peripheral configuration similar to that shown in U.S. Pat. No. 4,653,748. This disc includes a configured periphery as described in the aforementioned patent, and the patient places one foot upon the disc while grasping the hand holding means above the platform.

The universal joint support of the disc permits the patient to nutate the disc about its periphery and apply weight to the platform through the disc outer periphery at various distances from the shaft axis as determined by the disc configuration. The upper surface of the platform includes a plurality of switches sensitive to engagement by the disc periphery wherein the angular point of engagement of the disc periphery on the platform may be accurately electronically determined. Accordingly, by the use of the disc operated switches and the platform weight sensors the amount of weight exerted by the patient through the disc upon the platform may be very accurately located and determined.

The electronic output generated by the platform sensors and the switches is fed into a computerized system having a software program capable of analyzing the input and producing an output to a cathode ray tube (CRT) monitor permitting an immediate visual observation of the results of the disc movement and weight imposed upon the disc and platform. This analysis permits various lower limb conditions to be immediately ascertained, and the program, when using a color monitor, permits various shades of color to become visible, the color being proportionate to the amount of weight being applied to the platform at various angular positions relative to the shaft axis.

The shaft is supported upon elevator structure which permits the shaft to be raised and lowered relative to the platform which will change the angle of operation of the foot supporting disc, i.e. the higher the disc is above the platform the greater the angle of disc displacement required to engage the disc periphery with the platform upper surface. Thus, in initial stages of rehabilitation the foot supporting disc may be located relatively close to the platform minimizing the flexing of the ankle and lower extremity required to engage the disc periphery with the platform. As rehabilitation progresses, the shaft and disc may be raised further from the platform to increase the extent of ankle movement required.

The computerized analysis and output permits instantaneous visualization of the operation of the biomechanical analysis system and, of course, by the use of internal memory or use of a printer a copy of each patient's testing may be readily retained for comparison with subsequent testing. Depending on whether the nutation of the foot supporting disc is to be achieved primarily by ankle movement, or by movement of substantially the whole lower leg or extremity a wide variety of conditions of the lower extremity may be readily observed and analyzed, and the practice of the invention permits complete assessment of the function of the lower extremity and the patient can be actively involved in his own rehabilitation and can realize his progress as it occurs. A further advantage of the invention results from the documentation achievable with the invention with respect to insurance claims.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENT

Figure 1:
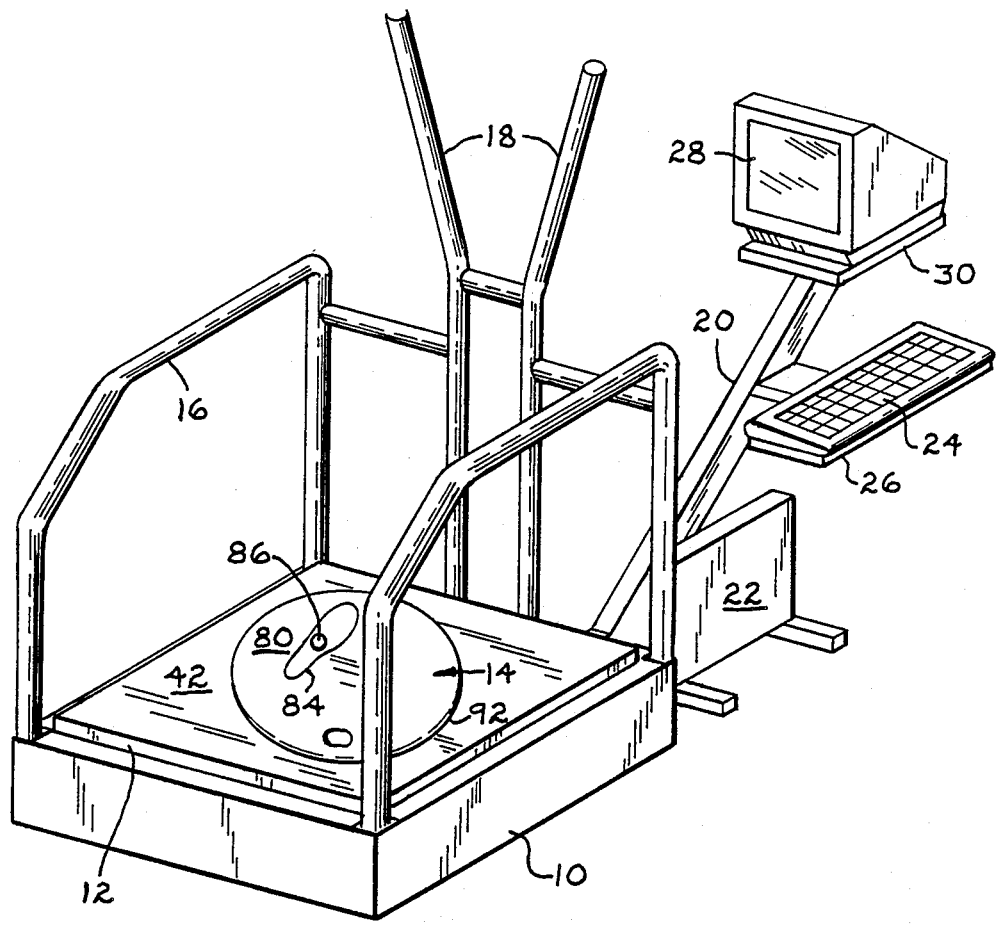
FIG. 1 is a front perspective view of a biomechanical analysis system in accord with the invention illustrating the computer equipment located adjacent the patient supporting frame apparatus.
Figure 2:
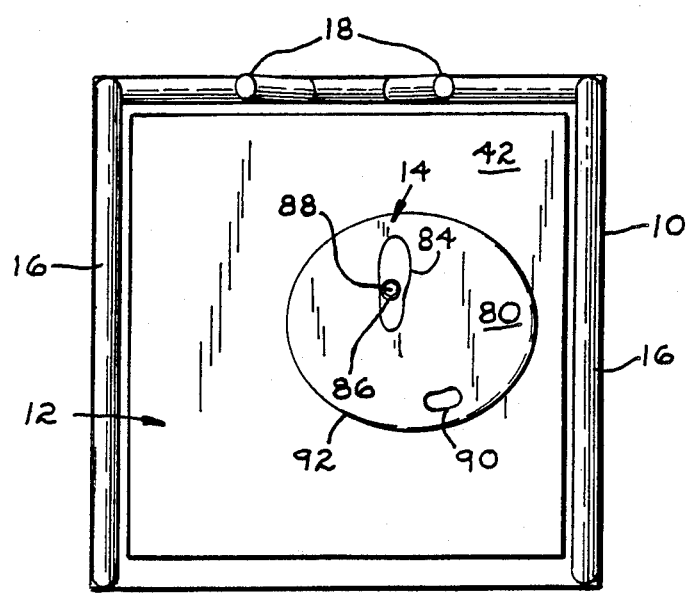
FIG. 2 is a top plan view of the frame of the apparatus.

The basic components of apparatus practicing the inventive concepts is best shown in FIG. 1. The patient supporting apparatus includes a frame 10 having a weight sensing platform 12 mounted thereon, and the foot supporting disc 14 is located above the platform in spaced relationship thereto. A plurality of handrail devices extend upwardly from the frame about the platform including side rails 16 and vertically extending Y-shaped rails 18 are centrally located so as to be easily grasped by a patient standing upon the disc 14 with one foot.

The computerized apparatus associated with the system may be mounted upon a separate frame 20 and is connected to the electronic system within the frame by a flexible conductor, not shown. Upon the frame 20 the computer 22 is mounted which includes a hard disc memory and a keyboard control 24 is mounted upon frame table 26 while the cathode ray tube (CRT) monitor 28 is mounted upon the frame table 30 and positioned as to be readily observable by the patient standing upon the disc 14.

Figure 7:
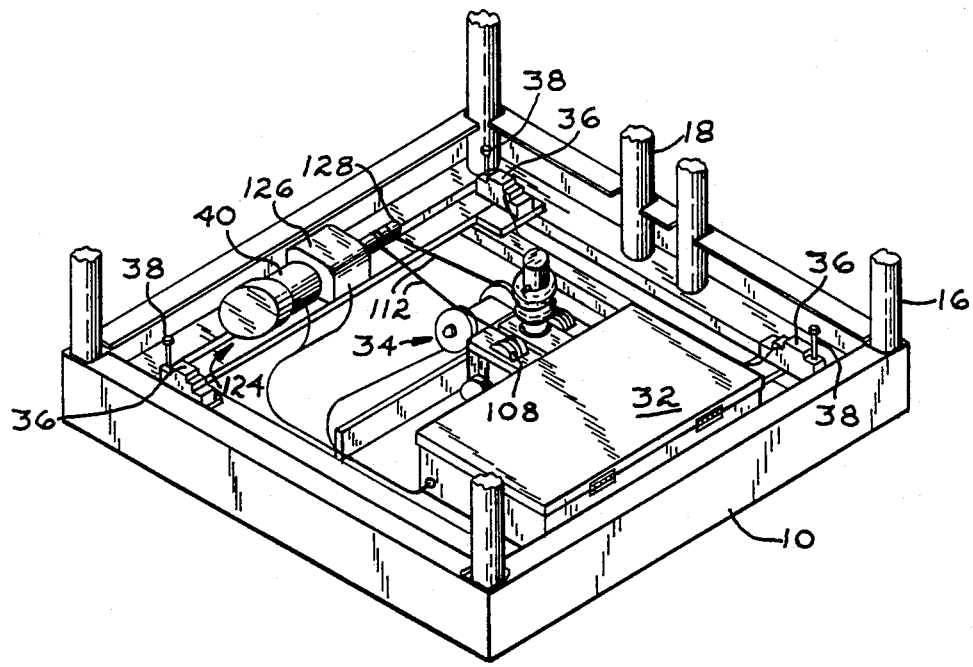
FIG. 7 is a perspective view of the lower frame, the platform being removed for purpose of illustration.
Figure 8:
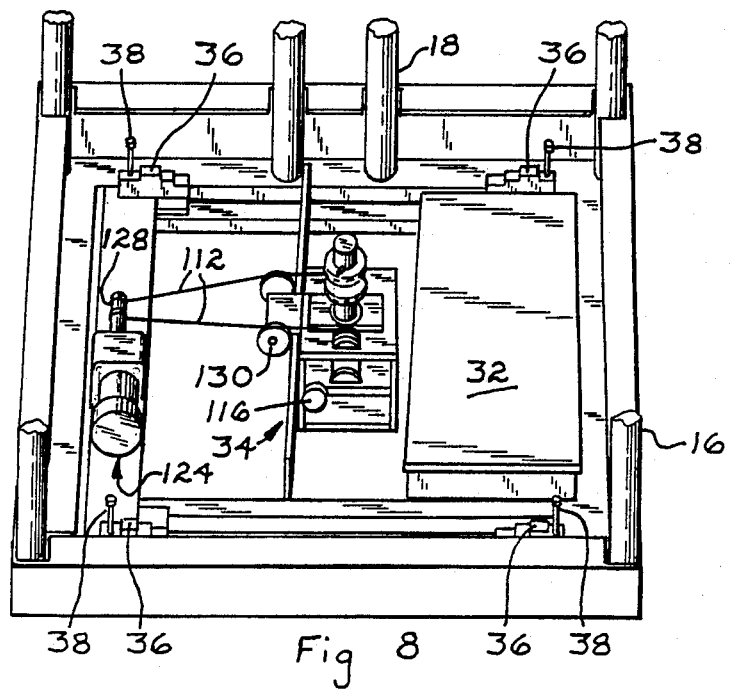
FIG. 8 is another perspective view of the lower frame, with the platform removed, taken from another angle of view.

As best illustrated in FIGS. 7 and 8 the frame 10 defines a rectangular cavity in which the primary mechanical apparatus of the system of the invention is located. This apparatus includes a circuit box 32 in which various electronic components such as relays, printed circuit boards, and the like are located, and the box includes a removable cover for access. The disc shaft supporting structure is centrally located as generally represented at 34, and this structure will be described in greater detail later.

A platform supporting weight sensing sensor 36 is located a each interior corner of the frame 10. Each of the four weight sensors 36 includes a vertically extending post 38 for engaging and supporting the platform 12, and the sensors very accurately determine the amount of weight imposed upon the sensor and produces an electrical signal proportional to such weight.

An electric winch motor, generally indicated at 40, is also mounted within the frame and is mechanically associated with the shaft support 34 as later described.

Figure 5:
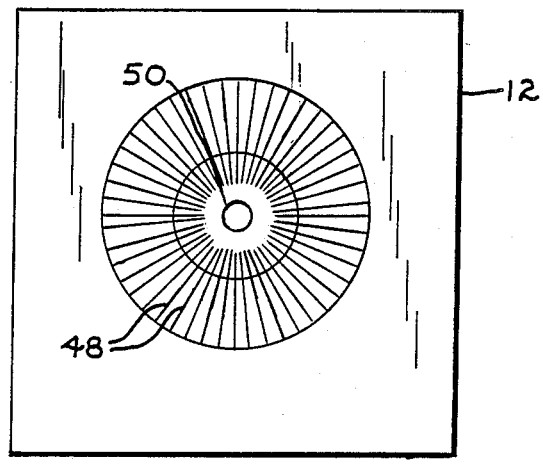
FIG. 5 is a top plan view of the upper surface of the platform, the platform covering being removed to illustrate presence of the switches located therebelow.
Figure 6:
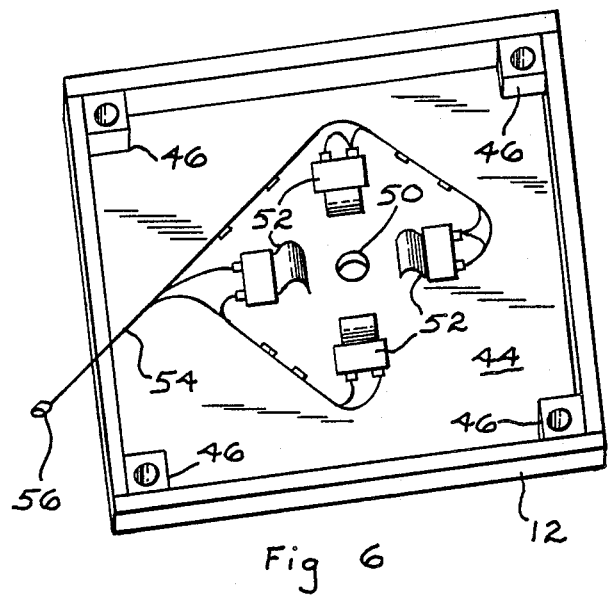
FIG. 6 is a perspective view of the underside of the platform.

The platform 12 is of a generally square configuration having an upper surface 42 and an under surface 44. The dimensions of the platform are such that the platform will freely fit within the inner cavity configuration of the frame 10, and the platform undersurface includes four pads 46 constituting recesses for receiving the upper ends of the weight sensor posts 38 wherein the platform is solely supported on the weight sensor posts in its normal operating condition. The upper surface 42 of the platform consists of a flexible covering, such as a thin rubberized sheet, and a plurality of elongated linear switches 48 are located below the sheet on the upper side of the platform, such switches being apparent in FIG. 5. The switches 48 are radially arranged about the central hole 50 defined through the platform, and the switches are of such a nature that a vertical force imposed upon a linear switch will close the switch completing the circuit therethrough. The underside 44 of the platform 12 is shown in FIG. 6 wherein four switch connectors 52 are illustrated feeding into the primary conductor 54 having connector 56 which plugs into electronic apparatus located within the circuit box 32. Preferably, 120 switches 48 are mounted upon the upper side of the platform 12 each representing approximately three degrees of angular displacement about the axis of the hole 50 for a purpose which will be later appreciated.

The shaft supporting apparatus 34 includes a vertically disposed shaft 58 located within a tubular sleeve 60. The sleeve includes a thrust bearing 62, FIG. 10, which supports the enlarged cylindrical head 64 of the shaft, and the head includes a universal joint or knuckle 66 which includes pivot axes 68 and 70 disposed at 90° to each other whereby the joint 66 is capable of rotating toward and away from the viewer, FIG. 10, or to the right or left, or combinations thereof. The universal joint 66 includes an upper stud 72 having a radial key 74 extending therefrom and a shoulder 76 adjacent the key and stud constitutes the support surface for the foot supporting disc 14 as later described. A flexible rubber boot 78, FIG. 9, encompasses the universal joint to protect the same from foreign matter and insure ease of operation.

The foot supporting disc 14 includes a first side 80 and a second side 82. These sides are mirror images of each other and each includes the outline 84 of a footprint so that when the left leg is being tested side 80 will be disposed upwardly, and visible to the patient, and when the right leg or extremity is being tested the disc is assembled to the shaft 58 so that the side 82 is directed upwardly and visible to the patient. Each of the sides includes a visible outline of the appropriate foot for designating the location of the foot during use.

The disc 14 is preferably formed of a synthetic plastic material, and is usually molded. An insert 86 is molded into the disc having a cylindrical opening 88 for closely receiving the shaft stud 72, and a key recess is defined therein whereby the key 74 will associate with the recess to prevent relative rotation between the disc and the stud. A hand opening 90 is preferably formed in the disc for facilitating handling or carrying of the disc.

The periphery 92 of the disc 14 corresponds to the configuration of the BAPS device disclosed in U.S. Pat. No. 4,653,748. This non-circular configuration of the disc in conjunction with the placing of the foot at the indicated position, is correlated to the computer program so as to permit the desired analysis during operation. The radial length of the switches 48 with respect to the platform hole 50 is sufficient to permit the disc periphery 92 to overlap the switches at all nutating positions of the disc, and it is to be understood that it is the periphery of the disc 14 which sequentially operates the switches 48 during analysis, testing and exercise.

Figure 11:
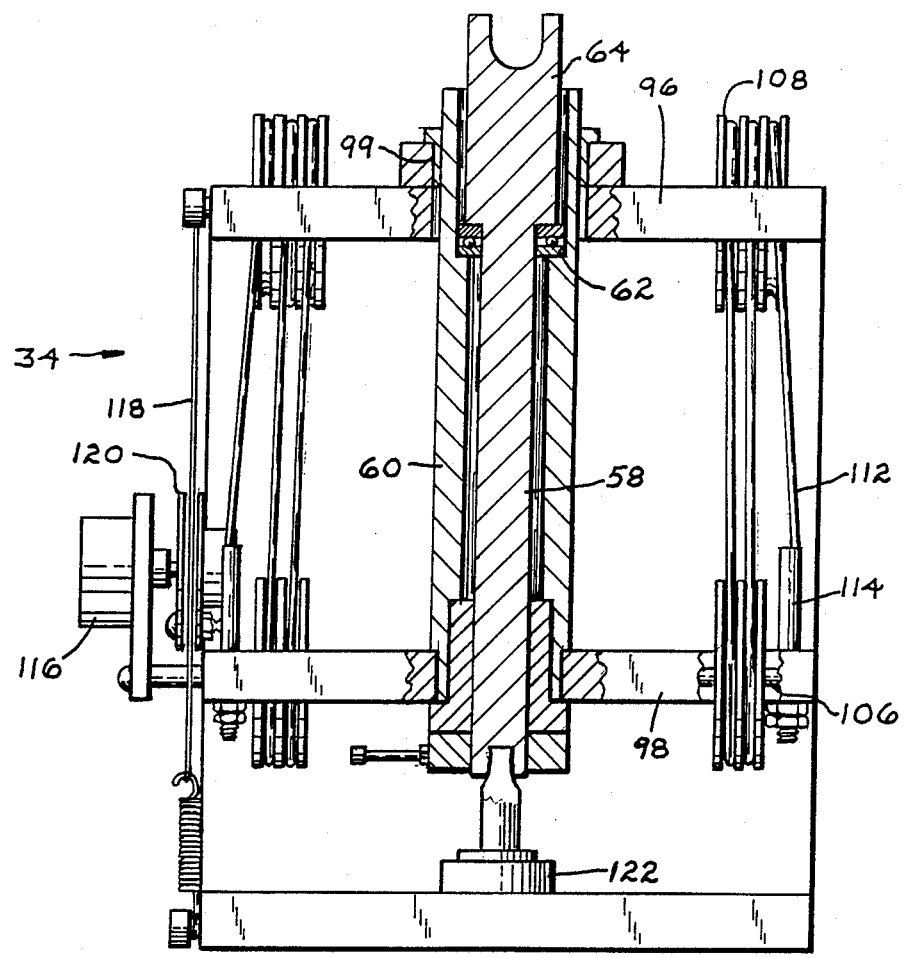
FIG. 11 is an enlarged, elevational partially sectional view of the shaft and elevator structure as taken along section 11—11 of FIG. 9, the universal joint not being illustrated.
Figure 9:
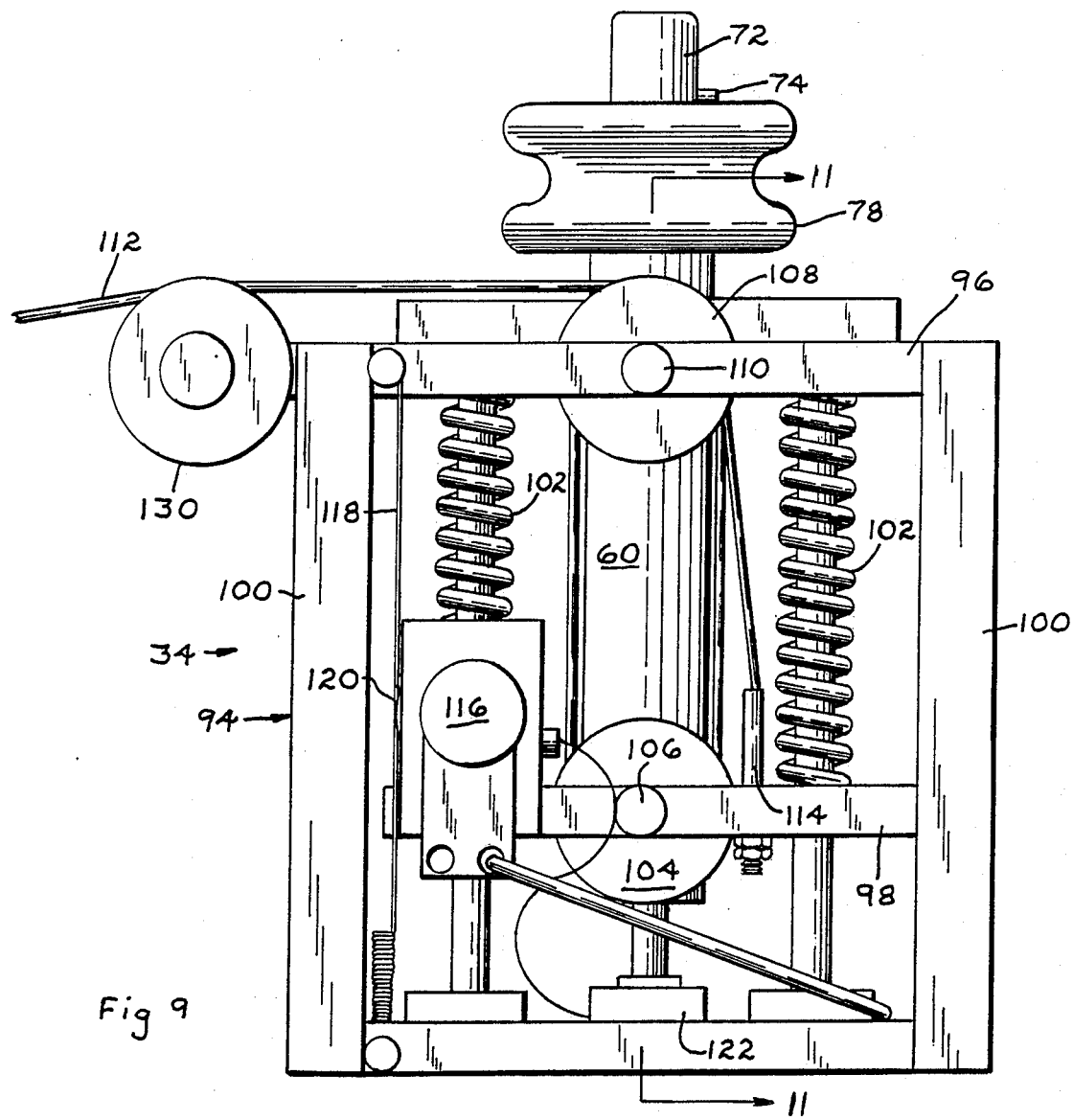
FIG. 9 is an enlarged elevational view of the shaft and elevator structure.
Figure 10:
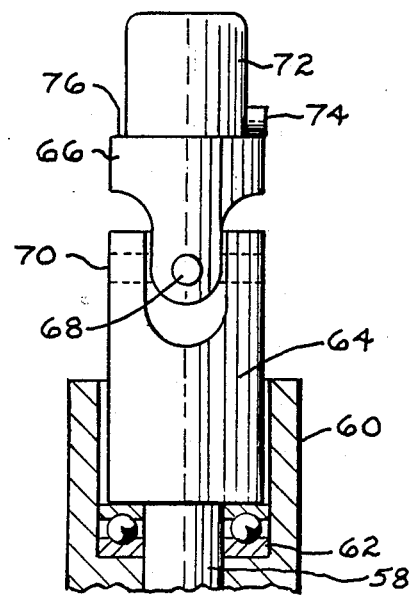
FIG. 10 is an enlarged, partial elevational view, partially sectioned, of the shaft, universal joint and thrust bearing.

The shaft support structure indicated at 34 includes a framework 94, FIGS. 9 and 11, which includes an upper guide block 96 and a lower guide block 98. The upper guide block 96 is stationery, and the sleeve 60 is slidably mounted within a bearing 99 mounted in block 96. The lower guide block 98 is vertically movable between the framework columns 100 and is affixed to the lower end of the sleeve 60 as will be apparent from FIG. 11. The lower guide block 98 is interconnected to upper block 96 by a plurality of counterbalancing tension springs 102, and the guide block 98 is raised and lowered through a pair of block and tackle systems which includes lower pulleys 104 rotatably mounted on the guide block by shafts 106 located on opposite sides of the sleeve 60. Upper pulleys 108 are rotatably mounted upon block 96 upon shafts 110 in alignment with pulleys 104, and each of the pulleys contain a plurality of grooves for receiving cable 112 which is threaded upon the pulleys in known block and tackle manner. The end of the cable 112 is anchored to guide block 98 by connector 114, FIG. 9.

Vertical movement of the sleeve 60 and shaft 58 and lower guide block 98 is sensed by electronic potentiometer 116 which is mounted on block 98 and operatively connected to a reference cable 118 interposed between the upper and lower regions of the framework 94. As the lower guide block 98 is raised and lowered the potentiality pulley 120 associated with the cable 118 rotates producing an electrical signal by the potentiometer 116 which is fed into the electronic circuit box 32.

The rotative position of the shaft 58 is also electronically indicated by an electronic direction indicating sensor device generally indicated at 122 which is affixed to the lower end of the shaft 58, FIG. 11. Thus, rotative movement of the shaft 58 will be sensed by the sensor 122 which will feed an electronic signal into the box 32 having a value indicating the rotational positon of the shaft to the frame 10.

Raising and lowering of the guide block 98, sleeve 60, and shaft 58 is accomplished through an electrical winch device generally indicated at 124. The winch includes the reversible electric motor 40, driving a transmission 126 connected to a drum 128 for operating the cables 112 associated with each of the block and tackle systems affixed to the guide blocks. Idler guide pulleys 130 are rotatably mounted upon the upper part of the framework 94 to prevent chaffing of the cables during operation.

The vertical position of the guide block 98 and shaft 58 will be determined by how much of the cables 112 is wound upon the winch drum 128. Rotation of the drum 128 in a direction to wind the cables thereupon will tension the cables 112 and raise the guide block 98 through the block and tackle support for the guide block and shaft. The presence of the counterbalance springs 102, and the reduction achieved by the transmission 126, and the mechanical advantage of the block and tackle systems permit a relatively small electric motor 40 to be used to raise and lower the shaft 58 even if a patient is standing upon the disc 14.

Figure 3:
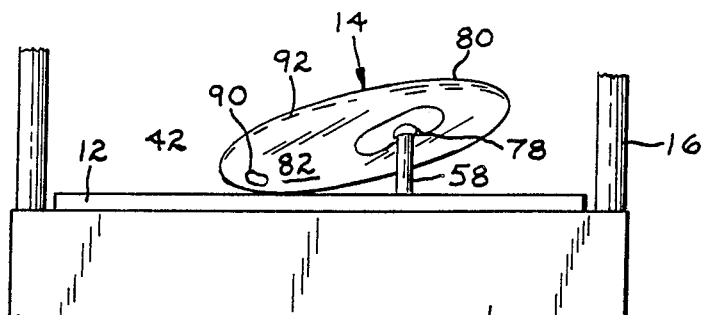
FIG. 3 is a partial elevational view of the platform and foot supporting disc, the disc supporting shaft being shown in an elevated condition.
Figure 4:
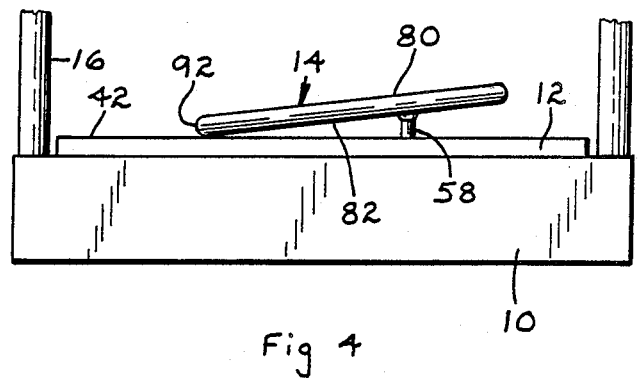
FIG. 4 is a view similar to FIG. 3, the disc supporting shaft being shown in a lowered condition.

In use, the operator initially determines the desired vertical orientation of the disc 14 to the platform 12, and this positioning of the shaft is achieved by entering the appropriate information into the computerized system through the keyboard 24. If it is desired to test the lower extremity for a high degree of flexibility the shaft 58 will be raised close to its upper limits by winding a maximum amount of the cables 112 upon the drum 128 wherein the foot supporting disc 14 will be highly elevated as shown in FIG. 3. If it is desired that a lesser movement of the ankle and lower extremity occur during testing the winch drum 128 will be unwound to permit the block and tackle devices to lower the guide plate 98 and lower the shaft 58 and disc 14, as shown in FIG. 4.

The patient places his left or right foot upon the disc 14 upon the footprint outline 84 indicated thereon, whether the right or left foot is to be employed is clearly indicated by the configuration of the footprint outline on the disc. Thereupon, the patient raises the other leg so that his entire weight is supported upon the disc 14, and the hand rails 18 are grasped to permit the patient to retain his balance during the testing. Of course, the patient's weight is not to be applied to the hand rails as such would produce incorrect readings.

Under instruction from the operator, the patient then begins to nutate or flex the ankle or lower extremity in a single rotative direction to progressively and sequentially nutate the disc 14 so that sequential portions of the disc periphery 92 engage the platform 12 and actuate sequential switches 48. It will be appreciated that, normally, at all times, one portion of the disc periphery 92 will be engaging the platform and that the foot supporting disc 14, at no time during testing, will be maintained in a horizontal position so as not to engage the platform except in a balance test wherein the patient goal is to not touch the edge of the platform to any switches.

The patient, by the shifting of weight, and flexing of the ankle, nutates the disc 14 about the axis of the shaft 58, and the axis of the shaft 58 is preferably, substantially in alignment with the length of the patient's leg. As the disc 14 nutates different portions of its periphery 92 will sequentially engage the platform and sequentially apply pressure to the platform and sequentially close adjacent switches 48 as the nutation continues. Nutation may proceed at a relatively rapid rate, i.e. one "revolution" per second, or may proceed at a slower rate depending on the capabilities of the patient.

As the weight of the patient is applied to the platform by the disc periphery 92 the value of such weight will be immediately sensed by the spaced platform supporting sensors 36. The sensor 36 closest to the point of engagement of the disc periphery will record the greatest weight, and as the disc nutates the weight supported by each of the sensors 36 will rapidly vary, and the output of each of the sensors is instantaneously fed into the computer 22.

In addition to the platform sensors 36 feeding signals into the computer, the sequential closing of the switches 48 due to the pressure of the periphery of the disc also feeds signals into the computer to accurately determine the location of the forces being applied to the platform.

Figure 12:
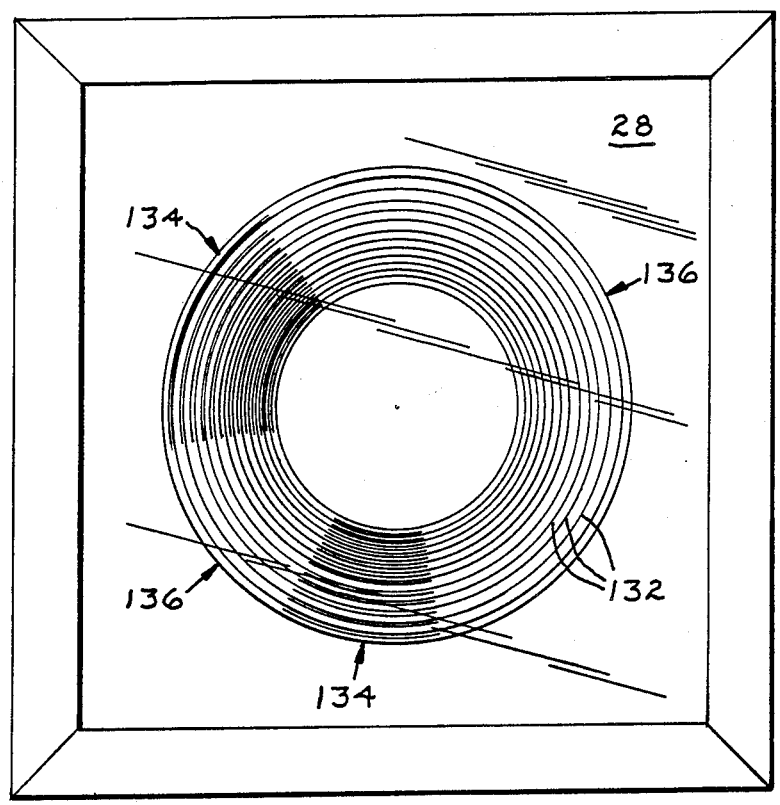
FIG. 12 is a schematic illustrative view of a cathode ray display tube illustrating a typical display of the biomechanical analysis system in accord with the invention.
Figure 13:
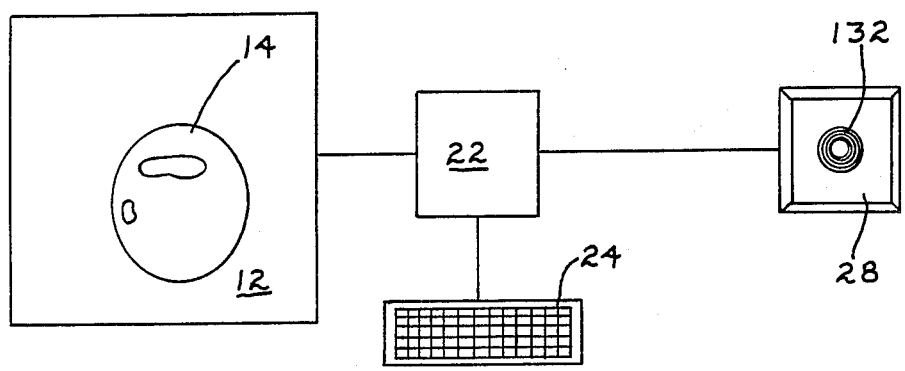
FIG. 13 is a schematic block diagram illustrating the mechanical and electronic components of the system.

During the testing, the program sequentially radially places the output upon the recording and monitoring equipment in a spiral manner so that the result has a three-dimensional aspect. For instance, with respect to FIG. 12, a plurality of substantially concentric spiral rings 132 are illustrated, each ring representing a rotation of disc pressure as applied to the platform 12 and switches 48 by a complete "revolution" of the nutation movement of the disc 14. Each subsequent disc rotation produces another ring under the control of the program. Because the portion of the patient's weight being borne by the shaft 58 and that being applied to the peripheral disc and platform varies because of the characteristics of the lower extremity and ankle the pressure being applied to the platform varies during the circumference of each circle 132. Preferably, the monitor 28 is of the color type, and the program produces a different color and hue of signal in accordance with the pressure being applied to the platform by the patient. Accordingly, at the end of the test the plurality of rings 132 will produce a pattern somewhat similar to that represented in FIG. 12 wherein portions of the pattern will be of different colors, such as at 134, as compared to other portions of the pattern, such as at 136, indicating to the observer the exact ability of the extremity to distribute weight to the platform at various angular relationships to the axis of the leg. This information can be compared to "correct" weight distribution of a normal extremity, and the device of the application produces instantaneously analysis of the condition of the extremity during testing.

The output of the apparatus of invention may be printed to produce a hard copy of the results of the testing, and the apparatus, in addition to be used for testing and analysis, may also be used for exercise wherein the patient may, during a single use of the apparatus observe a marked increase in flexibility and a change in weight distribution, and the operator, by coaching the patient, is able to advise the patient as to those weight distributions that are most beneficial and the operator can observe if the patient is "favoring" the extremity at certain angular orientations thereof.

Preferably, the computer program permits the monitor to illustrate a plurality of sequential tests simultaneously to permit the user to compare consecutive test results and directly observe improvement or recession of the treatments.

The apparatus of the invention permits a much higher degree of accuracy in the testing and recording of the analysis of the lower extremity, and the sensitivity of the apparatus provides significantly improved assessment procedures over those previously available.

It is appreciated that various modifications to the inventive concepts may be apparent to those skilled in the art without departing from the spirit and scope of the invention.

We claim:

1. A method of biomechanically analyzing the physical characteristics of a lower limb comprising the steps of:
    (a) placing the foot upon a support capable of universal deviation about a vertical axis,
    (b) sequentially applying weight upon said support at different angular locations with respect to said axis,
    (c) sensing the extent of said weight as applied at said angular locations to produce a plurality of weight-/location values with respect to said axis, and
    (d) recording said values to permit analysis of the distribution of weight relative to said axis.

2. The method of biomechanical analysis as in claim 1 wherein:
    (a) the step of placing the foot upon the support comprising locating the foot on the support such that the lower leg is substantially coaxially aligned with said vertical axis.

3. The method of biomechanical analysis as in claim 1 wherein:
    (a) the step of sequentially applying weight upon said support comprises sequentially applying weight in a continuous unidirectional manner about said vertical axis.

4. The method of biomechanical analysis as in claim 1 wherein:
    (a) the step of sensing the extent of said weight comprises producing an electrical signal, and
    (b) the step of recording said values comprises electronically analyzing and recording said electrical signals.

5. The method of biomechanical analysis as in claim 4, including the steps of:
    (a) producing a visual display of said electrical signals.

6. A method of biomechanically analyzing the physical characteristics of a lower limb utilizing a support having a center of nutation comprising the steps of:
    (a) placing the foot upon the support in a predetermined position relative to the center of nutation, (b) sequentially applying weight upon said support at different angular locations with respect to said center of nutation,
(c) sensing the extent of said weight as applied at said angular locations to produce a plurality of weight-/location values with respect to said center of nutation, and
(d) recording said values to permit analysis of the distribution of weight relative to said center of nutation.

7. The method of biomechanical analysis as in claim 6 wherein:
(a) the step of placing the foot upon the support comprising locating the foot on the support such that the lower leg is substantially coaxially aligned with said vertical center of nutation.

8. The method of biomechanical analysis as in claim 6 wherein:
(a) the step of sequentially applying weight upon said support comprises sequentially applying weight in a continuous unidirectional manner about said vertical center of nutation.

9. The method of biomechanical analysis as in claim 6 wherein:
(a) the step of sensing the extent of said weight comprises producing an electrical signal, and
(b) the step of recording said values comprises electronically analyzing and recording said electric signals.

10. The method of biomechanical analysis as in claim 9 including the steps of:
(a) producing a visual display of said electrical signals.

11. A biomechanical analyzing system for the lower limb comprising, in combination, a frame, a foot support, universal support means maintaining said foot support upon said frame for universal movement about a vertical axis, weight sensing means mounted on said frame sensing the amount of weight imposed by said foot support on said frame and the angular location of the imposed weight relative to said axis and having a data output, and recording means recording said data output to permit the analysis of weight distribution relative to said axis.

12. In a biomechanical analysis system as in claim 11, said weight sensing means comprising a platform.

13. In a biomechanical analysis system as in claim 12, said foot support being mounted above said platform and said universal support means extending through said platform.

14. In a biomechanical analysis system as in claim 13, said foot support comprising a disc having a periphery, said platform having an upper surface disposed toward said disc, a plurality of electric switches mounted on said platform upper surface adapted to be selectively engaged and operated by said disc periphery, said switches being connected to said weight sensing means data output.

15. In a biomechanical analysis system as in claim 14, said disc periphery having a non-circular configuration related in shape to the normal movements of the human ankle.

16. In a biomechanical analysis system as in claim 13, elevator means supporting said foot support on said frame for adjusting the vertical position of said foot support and regulating the vertical spacing between said foot support and said platform.

17. In a biomechanical analysis system as in claim 11, hand hold means mounted on said frame and vertically extending above said foot support.

18. A biomechanical analyzing system for the lower limb comprising, in combination, a frame, a platform, a plurality of spaced electronic weight sensors mounted on said frame supporting said platform each having an independent output signal, a vertically oriented shaft having an axis mounted on said frame having an upper end extending through and above said platform, a universal joint mounted on said shaft upper end, a foot support mounted on said universal joint for universal nutating movement about said axis, means transferring weight imposed on said foot support in a angular manner about said axis to said platform, and recording means sensing said weight sensor output signals, said weight sensors being angularly related about said shaft axis whereby said recording means records weight application to said platform about said axis.

19. In a biomechanical analysis system as in claim 18, said foot support comprising a disc having a periphery, located above said platform upon said universal joint said periphery comprising said means for transferring said weight and adapted to engage said platform upon said disc nutating about said axis to apply weight upon said platform about said axis.

20. In a biomechanical analysis system as in claim 19, said disc periphery having a non-circular configuration related in shape to the normal movements of the human ankle.

21. In a biomechanical analysis system as in claim 19, a plurality of electric switches defined on said platform located below said disc periphery and adapted to be selectively operated by said disc periphery to indicate the angular orientation of force applied to said platform relative to said axis, said switches being connected to said recording means.

22. In a biomechanical analysis system as in claim 19, elevator means supporting said shaft adapted to selectively vertically position said shaft, universal joint and foot support relative to said platform.

23. In a biomechanical analysis system as in claim 18, said recording means including a computer having an output, and a cathode ray tube receiving said computer output, said tube visually indicating the application of weight to said platform relative to said axis.

24. In a biomechanical analysis system as in claim 18, hand hold means mounted on said frame and vertically extending above said foot support.

* * * * *